(12) United States Patent
Singh et al.

(10) Patent No.: US 8,173,629 B2
(45) Date of Patent: May 8, 2012

(54) METHOD OF TREATMENT USING FATTY ACID SYNTHESIS INHIBITORS

(75) Inventors: Sheo B. Singh, Edison, NJ (US);
Michael R. Tota, Middletown, NJ (US);
Jun Wang, Millburn, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 443 days.

(21) Appl. No.: 12/311,005

(22) PCT Filed: Sep. 18, 2007

(86) PCT No.: PCT/US2007/020226
§ 371 (c)(1),
(2), (4) Date: Mar. 16, 2009

(87) PCT Pub. No.: WO2008/039327
PCT Pub. Date: Apr. 3, 2008

(65) Prior Publication Data
US 2010/0022630 A1    Jan. 28, 2010

Related U.S. Application Data

(60) Provisional application No. 60/846,467, filed on Sep. 22, 2006.

(51) Int. Cl.
*A61K 31/33* (2006.01)
(52) U.S. Cl. ......................... 514/183; 514/866
(58) Field of Classification Search .................. 514/183, 514/866
See application file for complete search history.

(56) References Cited

U.S. PATENT DOCUMENTS

| | | | |
|---|---|---|---|
| 2,891,091 | A | 6/1959 | Darrach et al. |
| 5,981,575 | A | 11/1999 | Kuhajda et al. |
| 6,365,610 | B1 | 4/2002 | Sasaki et al. |
| 2008/0306139 | A1 | 12/2008 | Basilio et al. |

FOREIGN PATENT DOCUMENTS

| WO | WO 2005/009391 | 2/2005 |
|---|---|---|
| WO | WO 2005/115400 | 12/2005 |
| WO | WO 2005/117590 | 12/2005 |

OTHER PUBLICATIONS

Liu et al., Acta Pharmacol. Sin., vol. 25 (2004), pp. 1052-1057, "Effects of a fatty acid synthase inhibitor . . . ".
Dridi et al., Am J. Physiol. Regul. Integr. Comp. Physiol., vol. 291 (2006), pp. R138-R147, "FAS inhibitor cerulenin reduces food intake and melanocortin receptor gene . . . ".
Kim et al., Am. J. Physiol. Endocrinol. Metab., vol. 283 (2002), pp. E867-E879, "Expression of FAS within hypothalamic neurons: . . . ".
Menendez et al., Int'l J. of Oncology, vol. 26 (2005), pp. 1507-1515, "The estrogenic activity of synthetic progestins used in oral contraceptives . . . ".
Menendez et al., Int'l J. of Oncology, vol. 24 (2004), pp. 1369-1383, "Overexpression and hyperactivity of breast cancer-associated fatty acid syndrome . . . ".
Menendez et al., Int'l J. of Oncology, vol. 24 (2004), pp. 591-608, "Novel signaling molecules implicated in tumor-associated fatty acid synthase-dependent . . . ".
Lowy, J. Clin. Investig., vol. 111 (2003), pp. 1265-1273, "Antimicrobial resistance: the example of *Staphylococcus aureus*".
Shirling et al., Int'l J. of Systematic Bacteriol., vol. 16 (1966), pp. 313-340, "Methods for characterization of Streptomyces species".
Thupari et al., Am. J. Physiol. Endocrinol. Metab., vol. 287 (2004), pp. E97-E104, "Chronic C75 treatment of diet-induced obese mice . . . ".
Milgraum et al., Clinical Canacer Research, vol. 3 (1997), pp. 2115-2120, "Enzymes of the fatty acid synthesis pathway are highly expressed . . . ".
Tu et al., Endrocrinology, vol. 146 (2005), pp. 486-493, "C75 alters central and peripheral gene expression to reduce food intake and increase energy expenditure".
Menendez et al., J. Of Cellular Biochem., vol. 94 (2005), pp. 857-863, "Does endogenous fatty acid metabolism allow cancer cells to sense hypoxia . . . ".
Menendez et al., Molecular Carcinogenesis, vol. 41 (2004), pp. 164-178, "Pharmacological inhibition of fatty acid synthase (FAS): . . . ".
Miller et al., NeuroReport, vol. 15 (2004), pp. 925-929, "Anorexigenic C75 alters c-Fos in mouse . . . ".
Leonhardt et al., Physiology & Behavior, vol. 83 (2004), pp. 645-651, "Fatty acid oxidation and control of food intake".
Ronnett et al., Physiology & Behavior, vol. 85 (2005), pp. 25-35, "Fatty acid metabolism as a target for obesity treatment".
Schmid et al., Biochem. and Biophys. Res. Comm., vol. 328 (2005), pp. 1073-1082, "Inhibition of fatty acid synthase prevents preadipocyte differentiation".
Nicot et al., Biochem. and Biophys. Res. Comm., vol. 325 (2004), pp. 660-664, "C75 activates malonyl-CoA sensitive and insensitive components . . . ".
Yang et al., J. of Pharmacol. & Exper. Therap., vol. 312 (2005), pp. 127-133, "C75 [4-Methylene-2-octyl-5-oxo-tetrahydro-furan-3- . . . ".
Takahashi et al., Endocrinology, vol. 145 (2004), pp. 184-193, "The anorexigenic fatty acid synthase inhibitor, C75, is a nonspecific neuronal activator".
Hu et al., J. Biol. Chem., vol. 280 (2005), pp. 39681-39683, "A role for hypothalamic malonyl-CoA in the control of food intake".
McCullough et al., J. Biol. Chem., vol. 280 (2005), pp. 20493-20502, "Pharmacological inhibition of AMP-activated protein kinase . . . ".
Kim et al., J. Biol. Chem., vol. 279 (2004), pp. 19970-19976, "C75, a fatty acid synthase inhibitor, reduces food intake . . . ".
Landree et al., J. Biol. Chem., vol. 279 (2004), pp. 3817-3827, "C75, a fatty acid synthase inhibitor, modulates AMP-activated protein kinase . . . ".
Loftus et al., Science, vol. 288 (2000), pp. 2379-2381, "Reduced food intake and body weight in mice treated with fatty acid synthase inhibitors".

(Continued)

*Primary Examiner* — Kevin E Weddington
(74) *Attorney, Agent, or Firm* — Baerbel R. Brown; John C. Todaro

(57) ABSTRACT

The present invention relates to natural products that possess fatty acid synthesis inhibitor activity and can be used to treat and prevent diseases such as obesity, cancer, diabetes, fungal infections, Mycobacterium tuberculosis infections, malarial infections and other apicomplexan protozoal diseases.

1 Claim, No Drawings

OTHER PUBLICATIONS

Bentebibel et al., Biochemistry, vol. 45 (2006), pp. 4339-4350, "Novel effect of C75 on carnitine palmitoyltransferase I activity . . . ".

Wakil, Biochemistry, vol. 28 (1989), pp. 4523-4530, "Fatty acid synthase, a proficient multifuntional enzyme".

Hu et al., PNAS, vol. 102 (2005), pp. 3972-3977, "Effect of centrally administered C75, a fatty acid synthase inhibitor, on ghrelin secretion . . . ".

Kuhajda et al., Trends in Pharmacol. Sci., vol. 26 (2005), pp. 541-544, "The connections between C75 and obesity drug-target pathways".

Hu et al., PNAS, vol. 100 (2003), pp. 12624-12629, "Hypothalamic malonyl-CoA as a mediator of feeding behavior".

Gao et al., PNAS, vol. 100 (2003), pp. 5628-5633, "Effect of the anorectic fatty acid synthase inhibitor C75 on neuronal activity . . . ".

Thupari et al., PNAS, vol. 99 (2002), pp. 9498-9502, "C75 increases peripheral energy utilization and fatty acid oxidation . . . ".

Kumar et al., PNAS, vol. 99 (2002), pp. 1921-1925, "Differential effects of a centrally acting fatty acid synthase inhibitor . . . ".

Menendez et al., PNAS, vol. 101 (2004), pp. 10715-10720, "Inhibition of fatty acid synthase (FAS) suppresses HER2/neu (erbB-2) . . . ".

Kuhajda et al., PNAS, vol. 97 (2000), pp. 3450-3454, "Synthesis and antitumor activity of an inhibitor of fatty acid synthase".

Obici et al., Diabetes, vol. 51 (2002), pp. 271-275, "Central administration of oleic acid inhibits glucose . . . ".

Clegg et al., Diabetes, vol. 51 (2002), pp. 3196-3201, "Comparison of central and peripheral administration of C75 on food intake, . . . ".

Makimura et al., Diabetes, vol. 50 (2001), pp. 733-739, "Cerulenin mimics effects of leptin on metabolic rate, food intake, and body weight . . . ".

Zhou et al., Cancer Res., vol. 63 (2003), pp. 7330-7337, "Fatty acid synthase inhibition triggers apoptosis during S phase . . . ".

Rashid et al., Am. J. of Pathology, vol. 150 (1997), pp. 201-208, "Elevated expression of fatty acid synthase and fatty acid . . . ".

Alo et al., Cancer Res., vol. 77 (1996), pp. 474-482, "Expression of fatty acid synthase (FAS) as a predictor of recurrence . . . ".

Pizer et al., Cancer, vol. 83 (1998), pp. 528-237, "Fatty acid synthase expression in endometrial carcinoma".

Pizer et al., Cancer Res., vol. 56 (1996), pp. 2745-2747, "Inhibition of fatty acid synthesis induces programmed cell death . . . ".

Pizer et al., Cancer Res., vol. 60 (2000), pp. 213-218, "Malonyl-coenzyme-A is a potential mediator of cytotoxicity . . . ".

Menendez et al., Int. J. Cancer, vol. 115 (2005), pp. 19-35, "Pharmacological and small interference RNA-mediated inhibition . . . ".

Jensen et al., J. of Pathology, vol. 176 (1995), pp. 343-352, "The prognostic value of oncogenic antigen 519 (OA-519) expression and proliferative activity . . . ".

Menendez et al., Int'l J. of Molec. Med., vol. 15 (2005), pp. 33-40, "RNA interference-mediated silencing of the p53 tumor-suppressor protein . . . ".

Cha et al., Biochem. and Biophys. Res. Comm., vol. 317 (2004), pp. 301-308, "Long-term effects of fatty acid synthase inhibitor on obese mice: . . . ".

Pizer et al., Cancer Res., vol. 58 (1998), pp. 4611-4615, "Pharmacological inhibitors of mammalian fatty acid synthase suppress DNA . . . ".

Wortman et al., Nature Med., vol. 9 (2003), pp. 483-485, "C75 inhibits food intake by increasing CNS glucose metabolism".

Shimokawa et al., PNAS, vol. 99 (2002), pp. 66-71, "Effect of a fatty acid synthase inhibitor on food intake and expression . . . ".

METHOD OF TREATMENT USING FATTY ACID SYNTHESIS INHIBITORS

CROSS-REFERENCE TO RELATED APPLICATIONS

This application is a U.S. National Phase application under 35 U.S.C. §371 of PCT Application No. PCT/US2007/020226, filed Sep. 18, 2007, which claims priority from and the benefit of U.S. Provisional Application No. 60/846,467, filed Sep. 22, 2006.

BACKGROUND OF THE INVENTION

The present invention relates to a natural product that possesses fatty acid synthesis inhibitor activity and can be used to treat and prevent diseases such as obesity, cancer, diabetes, fungal infections, Mycobacterium tuberculosis infections, malarial infections and other apicomplexan protozoal diseases.

SUMMARY OF THE INVENTION

This invention describes the use of the natural product shown in formulas I and II as a fatty acid synthesis inhibitor:

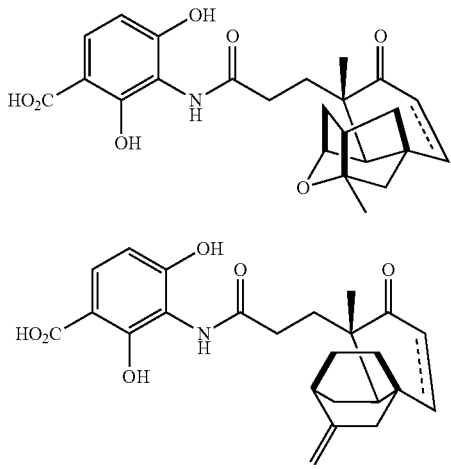

or pharmaceutically acceptable salts thereof, wherein ---- represents a bond that can be absent or present thereby denoting a single or double bond, respectively.

The natural products shown in formulas I and II can be administered to a patient in need thereof to treat, ameliorate the symptoms of, prevent and/or reduce the likelihood of suffering from obesity, cancer, diabetes, fungal infections, Mycobacterium tuberculosis infections, malarial infections and other apicomplexan protozoal diseases.

DETAILED DESCRIPTION OF THE INVENTION

This invention describes the use of the compounds of formula I or II or a pharmaceutically acceptable salt thereof as an agent to treat, ameliorate the symptoms of, prevent and/or reduce the likelihood of suffering from obesity, cancer, diabetes, fungal infections, Mycobacterium tuberculosis infections, malarial infections and other apicomplexan protozoal diseases. In preferred embodiments, the agents are used to treat, ameliorate the symptoms of, prevent and/or reduce the likelihood of suffering from obesity, diabetes, and/or cancer.

A number of studies have demonstrated surprisingly high levels of FAS expression (EC 2.3.1.85) (Rashid, A. et al. "Elevated expression of fatty acid synthase and fatty acid synthetic activity in colorectal neoplasia. *Am J Pathol* 150, 201-8 (1997)) in virulent human breast cancer (Alo, P. L. et al. Expression of fatty acid synthase (FAS) as a predictor of recurrence in stage I breast carcinoma patients" *Cancer* 77, 474-82 (1996) and Jensen, V. et al "The prognostic value of oncogenic antigen 519 (OA-519) expression and proliferative activity detected by antibody MIB-1 in node-negative breast cancer". *J Pathol* 176, 343-52 (1995)) aw well as other cancers (Rashid, A. et al. "Elevated expression of fatty acid synthase and fatty acid synthetic activity in colorectal neoplasia. *Am J Pathol* 150, 201-8 (1997) and Pizer, E. S. et al "Fatty acid synthase expression in endometrial carcinoma: correlation with cell proliferation and hormone receptors" *Cancer* 83, 528-37 (1998).

FAS expression has also been identified in intraductal and lobular in situ breast carcinoma, lesions associated with increased risk for the development of infiltrating breast cancer (Milgraum, L. Z. et al "Enzymes of the fatty acid synthesis pathway are highly expressed in in situ breast carcinoma" *Clin Cancer Res* 3, 2115-20 (1997).

FAS is the principal synthetic enzyme of FA synthesis, which catalyzes the NADPH-dependent condensation of malonyl-CoA and acetyl-CoA to produce predominantly the 16-carbon saturated free FA palmitate (Wakil, S. J. "Fatty acid synthase, a proficient multifunctional enzyme" *Biochemistry* 28, 4523-30 (1989)). Ex vivo measurements in tumor tissue have revealed high levels of both FAS and FA synthesis, indicating that the entire genetic program is highly active consisting of some 25 enzymes from hexokinase to FAS (Rashid, A. et al. "Elevated expression of fatty acid synthase and fatty acid synthetic activity in colorectal neoplasia. *Am J Pathol* 150, 201-8 (1997)). Cultured human cancer cells treated with inhibitors of FAS, including the fungal product cerulenin and the novel compound C75, demonstrated a rapid decline in FA synthesis, with subsequent reduction of DNA synthesis and cell cycle arrest, culminating in apoptosis (Pizer, E. S. et al. "Ihibition of fatty acid synthesis induces programmed cell death in human breast cancer cells" *Cancer Res* 56, 2745-7 (1996) and Pizer, E. S., et al "Pharmacological inhibitors of mammalian fatty acid synthase suppress DNA replication and induce apoptosis in tumor cell lines" *Cancer Res* 58, 4611-5 (1998).

These findings suggested a vital biochemical link between FA synthesis and cancer cell growth and a possible target for anticancer drug development (Pizer, E. S. et al. "Malonyl-coenzyme-A is a potential mediator of cytotoxicity induced by fatty-acid synthase inhibition in human breast cancer cells and xenografts" *Cancer Res* 60, 213-8 (2000); Kuhajda, F. P. et al. "Synthesis and antitumor activity of an inhibitor of fatty acid synthase" *Proc Natl Acad Sci USA* 97, 3450-4 (2000); Zhou, W. et al. "Fatty acid synthase inhibition triggers apoptosis during S phase in human cancer cells" *Cancer Res* 63, 7330-7 (2003); Menendez, J. A. et al "Novel signaling molecules implicated in tumor-associated fatty acid synthase-dependent breast cancer cell proliferation and survival: Role of exogenous dietary fatty acids, p53-p21WAF1/CIP1, ERK1/2 MAPK, p27KIP1, BRCA1, and NF-kappaB" *Int J Oncol* 24, 591-608 (2004); Menendez, J. A. et al. "Overexpression and hyperactivity of breast cancer-associated fatty acid synthase (oncogenic antigen-519) is insensitive to normal arachidonic fatty acid-induced suppression in lipogenic tissues but it is selectively inhibited by tumoricidal alphalinolenic and gamma-linolenic fatty acids: a novel mechanism by which dietary fat can alter mammary tumorigenesis" *Int J Oncol* 24, 1369-83 (2004); Menendez, J. A. et al. "Inhibition of fatty acid synthase (FAS) suppresses HER2/neu (erbB-2) oncogene overexpression in cancer cells" *Proc Natl Acad Sci USA* 101, 10715-20 (2004); Menendez, J. A., et al "Pharmacological inhibition of fatty acid synthase (FAS): a novel therapeutic approach for breast cancer chemoprevention through its ability to suppress Her-2/neu (erbB-2) oncogene-induced malignant transformation" *Mol Carcinog* 41, 164-78 (2004); Menendez, J. A. & Lupu, R. "RNA interference-mediated silencing of the p53 tumor-suppressor protein drastically increases apoptosis after inhibition of endogenous fatty acid metabolism in breast cancer cells" *Int J Mol Med* 15, 33-40 (2005); Menendez, J. A. et al "Pharmacological and small interference RNA-mediated inhibition of breast cancer-associated fatty acid synthase (oncogenic antigen-519) synergistically enhances Taxol (paclitaxel)-induced cytotoxicity" *Int J Cancer* 115, 19-35 (2005); Menendez, J. A. et al "Does endogenous fatty acid metabolism allow cancer cells to sense hypoxia and mediate hypoxic vasodilatation? Characterization of a novel molecular connection between fatty acid synthase (FAS) and hypoxia-inducible factor-1alpha (HIF-1alpha)-related expression of vascular endothelial growth factor (VEGF) in cancer cells overexpressing her-2/neu oncogene" *J Cell Biochem* 94, 857-63 (2005); Menendez, J. A. et al "The estrogenic activity of synthetic progestins used in oral contraceptives enhances fatty acid synthase-dependent breast cancer cell proliferation and survival" *Int J Oncol* 26, 1507-15 (2005)) Thus, an object of this invention is to provide a method for treating cancer by administering the compound of formula I to a patient in need thereof.

Since Loftus et al (Loftus, T. M. et al. Reduced food intake and body weight in mice treated with fatty acid synthase inhibitors. *Science* 288, 2379-81 (2000)) reported that C75 reduced mice food intake and body weight in 2000, tremendous efforts have been focused to determine its mechanism of action[4,20-48](Pizer, E. S., Lax, S. F., Kuhajda, F. P., Pasternack, G. R. & Kurman, R. J. Fatty acid synthase expression in endometrial carcinoma: correlation with cell proliferation and hormone receptors. *Cancer* 83, 528-37 (1998). oftus, T. M. et al. "Reduced food intake and body weight in mice treated with fatty acid synthase inhibitors" *Science* 288, 2379-81 (2000); Makimura, H. et al. "Cerulenin mimics effects of leptin on metabolic rate, food intake, and body weight independent of the melanocortin system, but unlike leptin, cerulenin fails to block neuroendocrine effects of fasting" *Diabetes* 50, 733-9 (2001); Shimokawa, T. et al "Effect of a fatty acid synthase inhibitor on food intake and expression of hypothalamic neuropeptides" *Proc Natl Acad Sci USA* 99, 66-71 (2002); Kumar, M. V. et al "Differential effects of a centrally acting fatty acid synthase inhibitor in lean and obese mice" *Proc Natl Acad Sci USA* 99, 1921-5 (2002); Thupari, J. N. et al "C75 increases peripheral energy utilization and fatty acid oxidation in diet-induced obesity" *Proc Natl Acad Sci USA* 99, 9498-502 (2002); Kim, E. K. et al. "Expression of FAS within hypothalamic neurons: a model for decreased food intake after C75 treatment" *Am J Physiol Endocrinol Metab* 283, E867-79 (2002); Clegg, D. J. et al "Comparison of central and peripheral administration of C75 on food intake, body weight, and conditioned taste aversion" *Diabetes* 51, 3196-201 (2002); Gao, S. & Lane, M. D. "Effect of the anorectic fatty acid synthase inhibitor C75 on neuronal activity in the hypothalamus and brainstem" *Proc Natl Acad Sci USA* 100, 5628-33 (2003); Wortman, M. D. et al "C75 inhibits food intake by increasing CNS glucose metabolism" *Nat Med* 9, 483-5 (2003); Takahashi, K. A. et al "The anorexigenic fatty acid synthase inhibitor, C75, is a nonspecific neuronal activator" *Endocrinology* 145, 184-93 (2004); Hu, Z. et al "Hypothalamic malonyl-CoA as a mediator of feeding behavior" *Proc Natl Acad Sci USA* 100, 12624-9 (2003); Landree, L. E. et al. "C75, a fatty acid synthase inhibitor, modulates AMP-activated protein kinase to alter neuronal energy metabolism" *J Biol Chem* 279, 3817-27 (2004); Thupari, J. N. et al "Chronic C75 treatment of diet-induced obese mice increases fat oxidation and reduces food intake to reduce adipose mass" *Am J Physiol Endocrinol Metab* 287, E97-E104 (2004); Kim, E. K. et al. "C75, a fatty acid synthase inhibitor, reduces food intake via hypothalamic AMP-activated protein kinase" *J Biol Chem* 279, 19970-6 (2004); Cha, S. H. et al "Long-term effects of a fatty acid synthase inhibitor on obese mice: food intake, hypothalamic neuropeptides, and UCP3" *Biochem Biophys Res Commun* 317, 301-8 (2004); Miller, I. et al "Anorexigenic C75 alters c-Fos in mouse hypothalamic and hindbrain subnuclei" *Neuroreport* 15, 925-9 (2004); Liu, L. H. et al. "Effects of a fatty acid synthase inhibitor on adipocyte differentiation of mouse 3T3-L1 cells" *Acta Pharmacol Sin* 25, 1052-7 (2004); Yang, N. et al. "C75 [4-methylene-2-octyl-5-oxo-tetrahydro-furan-3-carboxylic acid] activates carnitine palmitoyltransferase-1 in isolated mitochondria and intact cells without displacement of bound malonyl CoA" *J Pharmacol Exp Ther* 312, 127-33 (2005); Tu, Y. et al. "C75 alters central and peripheral gene expression to reduce food intake and increase energy expenditure" *Endocrinology* 146, 486-93 (2005); Nicot, C. et al. "C75 activates malonyl-CoA sensitive and insensitive components of the CPT system" *Biochem Biophys Res Commun* 325, 660-4 (2004); Leonhardt, M. & Langhans, W. "Fatty acid oxidation and control of food intake" *Physiol Behav* 83, 645-51 (2004); Schmid, B. et al "Inhibition of fatty acid synthase prevents preadipocyte differentiation" *Biochem Biophys Res Commun* 328, 1073-82 (2005); Hu, Z. et al "Effect of centrally administered C75, a fatty acid synthase inhibitor, on ghrelin secretion and its downstream effects" *Proc Natl Acad Sci USA* 102, 3972-7 (2005); McCullough, L. D. et al. "Pharmacological inhibition of AMP-activated protein kinase provides neuroprotection in stroke" *J Biol Chem* 280, 20493-502 (2005); Kuhajda, F. P. et al "The connections between C75 and obesity drug-target pathways" *Trends Pharmacol Sci* 26, 541-4 (2005); Ronnett, G. V. et al "Fatty acid metabolism as a target for obesity treatment" *Physiol Behav* 85, 25-35 (2005); Bentebibel, A. et al. "Novel effect of C75 on carnitine palmitoyltransferase I activity and palmitate oxidation" *Biochemistry* 45, 4339-50 (2006); Dridi, S. et al. "FAS inhibitor cerulenin reduces food intake and melanocortin receptor gene expression without modulating the other (an)orexigenic neuropeptides in chickens" *Am J Physiol Regul Integr Comp Physiol* 291, R138-47 (2006); Hu, Z. et al "A role for hypothalamic malonyl-CoA in the control of food intake" *J Biol Chem* 280, 39681-3 (2005)). Loftus et al., have suggested in their original paper that these compounds might, like leptin, act in part by modulating the hypothalamic neuropeptide gene expression. However, studies investigating this hypothesis revealed conflicting results. Indeed, Shimokawa et al. reported that a single intraperitoneal injection of C75 modulates the expression of hypothalamic orexigenic and anorexigenic neuropeptides in a manner similar to that of feeding and leptin. Cha et al. also showed that long-term treatment with C75 mimics the effect of leptin on hypothalamic neuropeptide gene expression in mice, whereas Kumar et al. reported that repeated injections of C75 either have no effect on or regulate hypothalamic neuropeptide mRNA levels in a manner opposite to that of feeding and leptin. Makimura et al. also reported that repeated injections with cerulenin decreases body weight and increases metabolic rate in mice without modulating hypothalamic neuropeptide gene expression. These discrepancies might be related to the physiological context and models.

Fatty acid metabolism, including fatty acid synthesis and oxidation and fatty acids themselves (Obici, S. et al. "Central administration of oleic acid inhibits glucose production and food intake" *Diabetes* 51, 271-5 (2002)) provides another means through which the CNS can monitor energy status and regulate feeding behavior. All studies to date have found that C75 provokes dramatic and sustained weight loss. One component of this weight loss is increased fatty acid oxidation in peripheral tissues, which is probably a result of stimulation of CPT-1 activity by C75. Another component to the mechanism is probably initiated in the hypothalamus and linked to energy metabolism as evidenced by the recent studies implicating AMPK in C75 signaling (Landree, L. E. et al. "C75, a fatty acid synthase inhibitor, modulates AMP-activated protein kinase to alter neuronal energy metabolism" *J Biol Chem* 279, 3817-27 (2004); Kim, E. K. et al. "C75, a fatty acid synthase inhibitor, reduces food intake via hypothalamic AMP-activated protein kinase" *J Biol Chem* 279, 19970-6 (2004)). Thus, another object of this invention is to provide a method for treating obesity by administering the compound of formula I to a patient in need thereof.

The invention relates to methods of using the compounds of formula I and II described herein. As demonstrated herein, the compounds of formula I and/or II are useful for the treatment of cancer. Accordingly, in one embodiment, the invention relates to a method of treating cancer in a subject in need of treatment comprising administering to said subject a therapeutically effective amount of the compounds of formula I and/or II described herein.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The term "treating" in its various grammatical forms in relation to the present invention refers to curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

The compounds of formula I and/or II can be administered alone or in combination with one or more other therapies suitable for the disease or disorder being treated. Where separate dosage formulations are used, the compounds of formula I and II and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the phosphorus compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The compounds of formula I and/or II are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, lfulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN 10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydr0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

The compositions of the present invention are useful for the treatment or prevention of disorders associated with excessive food intake, such as obesity and obesity-related disorders. The obesity herein may be due to any cause, whether genetic or environmental. Thus, an object of this invention is the use of the compounds of formula I and/or II to reduce food intake and/or increase metabolic rate.

The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer, nicotine addiction, substance addiction and alcoholism. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholesterol, non-HDL cholesterol, triglyceride, HDL cholesterol or other lipid analyte profiles.

Prevention of diabetes mellitus refers to the administration of a compound or combination of the present invention to prevent the onset of diabetes in a subject at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds of formula I and/or II or combinations of the present invention to reduce or maintain the body weight of an obese subject Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

Compounds of Formula I and/or II may be used in combination with other drugs that are used in the treatment/prevention/suppression or amelioration of the diseases or conditions for which compounds of Formula I and/or II are useful. Such other drugs may be administered, by a route and in an amount commonly used therefor, contemporaneously or sequentially with a compound of Formula I and/or II. When a compound of Formula I and/or II is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I and/or II.

Examples of other active ingredients that may be combined with a compound of Formula I and/or II for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like), and compounds disclosed in WO 97/10813, WO 97/27857, WO 97/28115, WO 97/28137, and WO 97/27847; (iii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH2);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO 97/28149;

(h) PPAR α/δ agonists, such as muraglitazar, and the compounds disclosed in U.S. Pat. No. 6,414,002;

(i) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine; and (j) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, W002/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838;

(13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II or those described in WO 99/64002 and WO 00/74679; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin), and those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR146131, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57)11β HSD-1 (11-beta hydroxy steroid dehydrogenase type 1) inhibitor such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, and (89) Neurokinin-1 receptor antagonists (NK-1 antagonists) such as the compounds disclosed in: U.S. Pat. Nos. 5,162,339, 5,232, 929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharamecueitcally acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-

(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof. Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Examples of other anti-obesity agents that can be employed in combination with a compound of Formula I and/or II are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The pharmaceutically acceptable salts of the compounds used in this invention include the conventional non-toxic salts as formed, from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylene-diamine, trimethylamine, piperidine, pyrrolidine, benzylamine and the like, or a quaternary ammonium hydroxide such as tetramethylammonium hydroxide and the like.

The pharmaceutically acceptable salts can be synthesized from the compounds of this invention by conventional chemical methods. Generally, the salts are prepared by reacting the free acid with stoichiometric amounts or with an excess of the desired salt-forming inorganic or organic base in a suitable solvent or various combinations of solvents.

The compounds of this invention can be formulated in pharmaceutical compositions by combining compounds I or II with a pharmaceutically acceptable carrier. Examples of such carriers are set forth below.

The compound may be employed in powder or crystalline form, in liquid solution, or in suspension. It may be administered by a variety of means; those of principal interest include: topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the Compound, the virulence of the infection and other factors. Such matters, however, are left to the routine discretion of the physician according to principles of treatment well known in the anticancer and antiobesity arts.

The compositions for administration to humans per unit dosage, whether liquid or solid, may contain from about 0.01% to as high as about 99% of Compound I or II, one embodiment of the range being from about 10-60%. The composition will generally contain from about 15 mg to about 2.5 g of Compound I or II one embodiment of this range being from about 250 mg to 1000 mg. In parenteral administration, the unit dosage will typically include pure Compound I or II in sterile water solution or in the form of a soluble powder intended for solution, which can be adjusted to neutral pH and isotonicity.

One embodiment of the methods of administration of Compound I or II includes oral and parenteral methods, e.g., i.v. infusion, i.v. bolus and i.m. injection.

For adults, about 5-50 mg of Compound I or II per kg of body weight given one to four times daily is preferred. The preferred dosage is 250 mg to 1000 mg of the compound of formula I or II given one to four times per day depending on the need.

For children, a dose of about 5-25 mg/kg of body weight given 2, 3, or 4 times per day is preferred; a dose of 10 mg/kg is typically recommended.

The Compound of formula I and II are produced by cultivating a *Streptomyces* sp. microorganism in a suitable nutrient medium and then recovering the compound of this invention from the fermentation broth. There are two organisms relating to the compound of formula I, ATCC# PTA-5316 (Merck Culture Collection # MA7327) and ATCC# PTA-5317 (MA7331) and one organism relating to the compound of formula II, ATCC# PTA-5942 (MA7339) all identified as the eubacterium, *Streptomyces* sp. following taxonomic studies and deposited in the Merck Culture Collection.

The organisms have been placed on permanent deposit with the American Type Culture Collection (ATCC), 12301 Parklawn Drive, Rockville, Md., 20852 and have been assigned accession numbers ATCC# PTA-5316 (Merck# MA7327) and ATCC# PTA-5317 (Merck# MA7331) for the compound of formula I and ATCC# PTA-5942 (Merck (MA#) MA7339) for the compound of formula II.

Any restrictions relating to public access to the microorganism shall be irrevocably removed upon patent issuance. Although the use of these particular species is described in connection with this invention, there may be other species and mutants of the above organism capable of producing Compound I, and their use is contemplated in carrying out the process of this invention.

The compound of structural Formula I or II is produced by the aerobic fermentation of a suitable medium under controlled conditions via inoculation with a culture of the eubacterium, *Streptomyces* sp. The suitable medium is preferably aqueous and contains sources of assimilable carbon, nitrogen, and inorganic salts.

The medium employed for fermentation by the *Streptomyces* sp. is primarily the well-known Difco Tryptic Soy Broth, either alone or with added nutrients commonly used by those skilled in the art.

It should be noted that the nutrient media described herein are merely illustrative of the wide variety of media which may be employed and are not intended to limit the scope of this invention in any way.

The fermentation is conducted at temperatures ranging from about 10° C. to about 40° C.; however for optimum results it is preferred to conduct the fermentation at about 28° C. The pH of the nutrient medium during the fermentation can be about 5.5 to about 7.5.

It is to be understood that for the fermentative production of the compounds of this invention, the invention is not limited to the use of the particular *Streptomyces* sp. with ATCC accession numbers, ATCC# PTA-5316 (Merck# MA7327), ATCC#PTA-5317 (Merck# MA7331) and ATCC#PTA 5942 (Merck# MA7339). It is especially desired and intended that there be included in the scope of this invention the use of other natural or artificial mutants produced or derived from the described cultures, or other variants or species of the *Streptomyces* genus insofar as they can produce the compound of this invention. The artificial production of mutant species or strains of *Streptomyces* from ATCC# PTA-5316 (Merck# MA7327), ATCC#PTA-5317 (Merck# MA7331) and ATCC#PTA 5942 (Merck# MA7339) may be achieved by conventional, physical or chemical mutagens, for example, ultraviolet irradiation of the described culture, or nitrosoguanidine treatment and the like. Recombinant DNA techniques such as protoplast fusion, plasmid incorporation, chromosome fragment incorporation and the like also may prove useful.

Example 1

Production of Compound I

The same methods were applied for both ATCC#PTA-5316 (MA7327) and ATCC#PTA-5317 (MA7331).

TABLE 1

| Media composition | |
|---|---|
| Seed Medium | g/L |
| Soluble Starch | 20.0 |
| Dextrose | 10.0 |
| NZ Amine Type E | 5.0 |
| Beef Extract | 3.0 |
| Yeast Extract | 5.0 |
| Peptone | 5.0 |
| (pH adjust to 7.0) | |
| Calcium Carbonate | 1.0 |
| CLA (Corn meal Lactose Ardamine) (Production Medium, per L) | |
| Amberex pH | 5.0 g |
| Yellow Corn Meal | 40.0 g |
| Lactose | 40.0 g |
| P-2000 (antifoaming agent) | 1.0 mL |

A frozen suspension (2.0 mL) of a *Streptomyces* sp. ATCC# PTA-5316 (MA7327) was inoculated into a 250 mL baffled flask containing 50 mL of seed medium. The flask was incubated at 28.0° C. with an agitation of 220 RPM for 48 hours. The second stage seed was developed by inoculating 10 mL, of the first stage seed into a two liter non-baffled shake flask containing 500 mL of seed medium. The flask was incubated at 28.0° C. with an agitation of 180 RPM for 48 hours. A 75 liter scale Chemap fermenter containing 50 liters of the CLA production medium was inoculated with 1.5 liters from the second stage seed. Operating parameters for the 75 liter scale fermenter were: Temperature=28° C., Agitation=300 RPM, Airflow=30 slpm, and pressure=5 psig. The fermenter containing 43 L of broth was harvested after 9 days of incubation.

Isolation of Compound I

To a 43 L fermentation broth was added 29 L MeOH and was acidified to pH 3.0 to give a final volume of 72 L. This extract was filtered and the filtrate was directly charged on a 1.5 L amberchrome and eluted with a 40-100% aqueous MeOH gradient collecting 600 mL each fractions. Fractions 11-13 containing mainly compound I were pooled and concentrated to 200 mL mainly aqueous, which was diluted with 300 mL water to give a final volume of 500 mL. Solid sodium bicarbonate was added to raise the pH to 9.0. This solution was extracted three times with equal volumes of methylene chloride. The aqueous layer was acidified to pH 2.0 with 6 N HCl (hydrochloric acid) and extracted four times with equal volumes of methylene chloride and the combined extract (1900 cc) were concentrated to 2.6 g of semi-purified compound I.

The semi-purified material was dissolved in small volume of ethyl acetate and charged to a 500 cc silica gel column packed in 80:20; hexane-ethyl acetate. The column was washed with four column volumes of the hexane-ethyl acetate (8:2) followed by four column volumes of 80:20:0.5:0.5:0.5 of ethyl acetate:hexane:water:glacial acetic acid:methanol collecting 200 mL each fractions. Fractions 6-10 were pooled, concentrated under reduced pressure to give 1.24 g of compound I.

Large Scale Isolation Procedure of Compound I

A 5 liters fermentation broth was acidified with 4 N HCl and extracted with 2.5 liters of isopropyl acetate which was extracted with 300 ml of 5% aqueous solution of sodium bicarbonate. The bicarbonate layer was charged to a 150 mL amberchrome column and washed with water until pH of eluents were neutral. The column was washed with one column volume of 0.1N HCl and washed with water until the pH of eluents became neutral. The column was eluted with two column volumes each of 20, 40, 60, 80, 90 and 100% aqueous methanol. The compound I eluted in the 90 and 100% aqueous methanol fractions. The pooled fractions were concentrated under reduced pressure mainly to aqueous and extracted with equal volumes of methylene chloride (isopropyl acetate and ethyl acetate were equally effective). The organic layer was concentrated to dryness to afford 193 mg of compound I as an amorphous powder, which could be crystallized from hot nitromethane, isopropyl acetate, ethyl acetate or acetonitrile-water.

Physical Data of Compound I

Compound I was crystallized from nitromethane as buff colored needles, mp 220-223° C. (decomposition at 230° C.), UV (CH$_3$OH) $\lambda_{max}$ 227 ($\epsilon$ 28,167), 296 (4,825) nm, $[\alpha]^{23}{}_D$ −51.1° (c 0.135, CH$_3$OH), FTIR (ZnSe) 3400, 2964, 1713 (w), 1650, (br, strong), 1535, 1446, 1378, 1296, 1240, 1153, 1105, 1091, 1024, 953, 828, 791, 608 cm$^{-1}$, HEESIFTMS. Found: 442.1853; calcd for C$_{24}$H$_{27}$NO$_7$+H: 442.1866, ¹H NMR (500 MHz) C$_5$D$_5$N δ$_H$: 1.14 (3H, s), 1.40 (3H, s), 1.48 (3H, d, J=11 Hz), 1.57 (1H, dd, J=11.5, 6.5 Hz), 1.73 (1H, dd, J=10.5, 3 Hz), 1.81 (2H, brd, J=11.5 Hz), 1.90 (1H, m), 2.0 (1H, m), 2.20 (1H, t, J=6.5 Hz), 2.45 (1H, brs), 2.68 (1H, m), 2.75 (1H, ddd, J=14.5, 11.5, 5), 2.83 (1H, ddd, J=14.5, 11.5, 5.5 Hz), 4.49 (1H, t, J=3.5 Hz), 5.94 (1H, d, J=10 Hz), 6.37 (1H, d, J=10 Hz), 6.87 (1H, d, J=9 Hz), 8.12 (1H, d, J=9 Hz), 10.5 (1H, s);

¹³C NMR (125 MHz) C$_5$D$_5$N δ$_C$: 23.9, 25.1, 32.4, 32.8, 41.4, 43.7, 45.7, 46.8, 47.2, 47.4, 55.6, 77.1, 87.5, 107.8, 110.5, 115.9, 127.9, 130.1, 154.6, 158.5, 159.1, 175.0, 175.2, 203.8

Characterization of Culture

Observations of growth, general cultural characteristics and carbon source utilization were made in accordance with the methods of Shirling and Gottlieb (*Int. J. Syst. Bacteriol.* (1966) 16: 313-340). Coloration of the cultures was determined by comparison with color standards contained in the Methuen Handbook of Colour (A. Kornerup and J. H. Wauscher, Third Edition, 1978).

Chemical composition of the cells was determined using the methods of Lechevalier and Lechevalier (1980).

Fatty acid composition was determined using a modified sample preparation (Sasser, 1990). Analysis of fatty acid methyl esters (FAMEs) was carried out by capillary gas chromatography using a Hewlett Packard Model 6890N gas chromatograph/Microbial Identification System software (MIDI, Inc., Newark, Del.) equipped with a phenyl methyl silicone column (0.2 mm×25 m). Individual fatty acids identification was determined by the Microbial Identification System software.

The complete 16S rDNA sequence was determined from the 1500 bp PCR fragment obtained using primers 27f and 1525r (Lane, 1991). The PCR product was used as template in sequencing reactions using an ABI PRISM™ Dye Terminator Cycle sequencing Kit (Perkin Elmer). Partial sequences were assembled using the GCG Fragment Assembly System (Wisconsin Package, version 8) and sequences were aligned with the program CLUSTALW (Intelligenetics, Inc.). The phylogenetic analysis of the aligned sequences was performed using the maximum-parsimony analysis with the branch-and-bound algorithm of the Phylogeny Using Parsimony Analysis (PAUP) program version 4.0. (Swofford, 1993).

Source

The strain ATCC# PTA-5316 (MA7327) was obtained from a soil collected in Eastern Cape, South Africa. The soil sample was associated to the rhyzosphere of *Manulea obovbata*, in a coastal zone of fynbos and dunes. The strain was isolated after serial dilution of the soil sample and plating on starch casein agar containing 20 ug/ml nalidixic acid.

The strain ATCC# PTA-5317 (MA7331) was isolated from a soil collected in Mallorca, Balearic Islands, Spain. The strain was isolated after pretreatment of the soil with 0.01% benzethonium chloride and plating on humic-acid based agar supplemented with 20 ug/ml novobiocin.

General Growth Characteristics

Strain ATCC PTA-5316 (MA7327) grows well on a range of agar media such as Yeast Malt Extract, Oatmeal, Glycerol Asparagine, Inorganic Salts Starch and Trypticase Soy agars at 28° C. The gross colonial morphology is typical of streptomycetes and its growth characteristics, including spore-mass colour, substrate mycelial pigmentation and the production of different pigments were recorded in different agar media (Table 2).

Colony Morphology (on Yeast Malt Extract Agar, ISP2)

Substrate mycelium initially whitish yellow turns brownish orange (5C6) after 21 days of incubation. The initial white aerial mycelium continues to develop after 21 days incubation turning yellow grey to finally become grey (5D2) with brownish wet exudate droplets.

Micromorphology

The spore-chain morphology was examined directly on the plates by light microscopy under 400× and 1000× magnification. Observations were made after 7, 14 and 21 days of cultivation on Yeast Malt Extract agar. The aerial mycelium arises from extensive branched substrate hyphae. Sparse branched aerial hyphae differentiate initially into short and irregular tight spore chain spirals. Sporophores are formed by less than 10-20 spores and with time tend to coalesce in a dark mucous mass of spores in older cultures. Similar morphologies were observed in most of the other test media but with different degrees of coalescence. On the contrary in the glycerol asparagines agar the strain grows as a sterile vegetative mycelium.

Strain ATCC#PTA-5317 (MA7331) grows well on the agar media tested such as Yeast Malt Extract, Oatmeal, Glycerol Asparagine, Inorganic Salts Starch and Trypticase Soy agars at 28° C. The gross colonial morphology is typical of streptomycetes and its growth characteristics were recorded in different agar media (Table 1).

Colony Morphology (on Yeast Malt Extract Agar, ISP2)

Substrate mycelium initially whitish yellow turns yellowish brown (5E7) after 21 days of incubation. The initial yellowish white aerial mycelium continues to develop after 21 days incubation to become uniformly grey (5E1).

Micromorphology

The spore-chain morphology was examined directly on the plates by light microscopy under 400× and 1000× magnification. Observations were made after 7, 14 and 21 days of cultivation on Yeast Malt Extract agar. An extensive aerial mycelium arises from a branched substrate hyphae. Sporophores are born at tip of aerial hyphae or in secondary branching hyphae. They form short and tight irregular spore chains with loop or coils, that after longer incubation time coalesce. Similar morphologies with different degrees of coalescence were observed in the other test media excepting in glycerol asparagine agar where the strain grows as a sterile vegetative mycelium.

Chemotaxonomic Analysis

The analysis of cell wall composition shows that strains ATCC# PTA-5316 (MA7327) and ATCC#PTA-5317 (MA7331) contain LL-A$_2$pm in whole-organism hydrolysates, a characteristic of *Streptomyces*. Strain ATCC# PTA-5316 (MA7327) contains glucose as major cell wall sugar whereas glucose and galactose are found as characteristic sugars in strain ATCC#PTA-5317 (MA7331). Both strains are rich in saturated straight-chain and iso- and anteiso-fatty acids but present completely different fatty acid patterns. Complete fatty acid compositions of are given in Table 2. The predominant fatty acids found in whole-cell methanolysates correspond to 15:0 anteiso and 16:0 iso, which are also typical of *Streptomyces*. All these chemotaxonomic analyses indicate that both strains correspond to members of the genus *Streptomyces*.

Physiological Properties

The strains present slightly different carbon utilization patterns (Table 4).

ATCC# PTA-5316 (MA7327): good utilization of D-glucose, sucrose, I-inositol, D-mannitol, D-fructose and raffinose; moderate utilization of D-xylose; poor utilization of L-arabinose and cellulose and no utilization of rhamnose.

ATCC#PTA-5317 (MA7331): good utilization of sucrose, D-xylose, I-inositol, D-fructose and raffinose; moderate utilization of D-glucose and D-mannitol; poor utilization of L-arabinose and no utilization of cellulose and rhamnose.

16S rDNA Sequence and Phylogenetic Analysis ping value (92%) and suggests that both isolates can be identified by different strains of the species *Streptomyces platensis*.

TABLE 2

Cultural characteristics of *Streptomyces* sp. ATCC# PTA-5316 (MA7327) and ATCC#PTA-5317 (MA7331) (21 days, 28° C.)

| Medium | Amount of growth | Aerial Mycelium | Soluble pigments | Substrate Mycelium |
|---|---|---|---|---|
| Strain ATCC#PTA-5316 (MA7327) | | | | |
| Yeast Extract Malt Extract (ISP2) | Abundant | Birch grey (5D2) with brown spots (5F4); extended aerial hyphae with very few short spore spirals | None | Brownish orange (5C6) |
| Oatmeal (ISP3) | Abundant | Grey (5D2) with extended brownish coalescence (5F4); Short sporophores arranged in tight short spirals (4-5 loops) on highly branched aerial mycelium | None | Yellowish brown (5E8) |
| Inorganic Salts Starch (ISP4) | Abundant | Grey (5D2) with extended brownish coalescence of spore mass (5F4); extended coalescence impairs observation of spore spirals. | None | Yellowish white in the borders (4A2) with brownish grey center (4E2) |
| Glycerol Asparagine (ISP5) | Sparse | none | None | Orange grey (5B2) sterile vegetative mycelium |
| Tyrosine Agar (ISP7) | Abundant | Yellowish brown in the edges and grey in the center (5B1); abundant short spore spirals in branched aerial hyphae | None | Dark brown (6F8) |
| Strain ATCC# PTA-5317 (MA7331) | | | | |
| Yeast Extract Malt Extract (ISP2) | Abundant | Uniformly grey (5E1), dense growth, extensive aerial mycelium with short and tight irregular spore chains forming loops and coils. Sporophores born in main and secondary aerial branches, coalescence. | None | Yellowish brown (5E7) |
| Oatmeal (ISP3) | Abundant | Brownish grey (5F2), extensive aerial mycelium, coalescence of spore chains. | None | Olive brown (4E4) |
| Inorganic Salts Starch (ISP4) | Abundant | Brownish grey (5F2), extensive aerial mycelium, coalescence of spore chains. | None | Olive brown (4D3/E3) |
| Glycerol Asparagine (ISP5) | Sparse | none | None | White(4B2), sterile substrate mycelium |
| Tyrosine Agar (ISP7) | Abundant | Grey (5C1), extensive aerial mycelium growth, short and tight spirals up to 3 turns born in main aerial hyphae, collapsing in coalescence | none | Greyish yellow (4B4) |

The complete 16S rDNA sequence has been determined for both strains. Sequences were aligned with *Streptomyces* nucleotide sequences from Genbank (AB045882) and the taxonomic position of both strains was determined by phylogenetic analysis of the aligned 16S rDNA sequences of 126 validated *Streptomyces* species. A phylogenetic tree based on these 16S rDNA sequences was built using the maximum parsimony method. Bootstrap replicates from each grouping was used as a measure of statistical confidence. A grouping found on 95% of bootstrap replicates was considered statistically significant.

The strains ATCC# PTA-5316 (MA7327) and ATCC#PTA-5317 (MA7331) appear in the same branch associated to the strain *Streptomyces platensis* ATCC 13865. This close relationship is highly supported by the bootstrap-

TABLE 3

Major fatty acids found in strains ATCC# PTA-5316 (MA7327) and ATCC# PTA-5317 (MA7331)

| Fatty acid | % of total fatty acids MA7327 | % of total fatty acids MA7331 |
|---|---|---|
| 14:0 iso | 11.54 | 2.50 |
| 15::0 | 2.14 | 4.12 |
| 15:0 iso | 8.95 | 25.02 |
| 15:0 anteiso | 14.77 | 11.25 |
| 15:0 anteiso 20H | 8.71 | 3.22 |
| 16::0 | 1.72 | 4.78 |
| 16:0 iso | 26.19 | 14.23 |
| 16:1 iso H | 7.78 | 2.15 |
| 16:0 iso 20H | 2.07 | 0.00 |
| 17:0 | 0.00 | 0.81 |

TABLE 3-continued

Major fatty acids found in strains ATCC# PTA-5316 (MA7327) and ATCC# PTA-5317 (MA7331)

| Fatty acid | % of total fatty acids MA7327 | % of total fatty acids MA7331 |
|---|---|---|
| 17:0 anteiso | 3.56 | 5.59 |
| 17:0 cyclo | 0.97 | 2.32 |
| 17:0 iso | 1.35 | 7.72 |
| 17:0 iso 20H | 0.00 | 0.73 |
| 17:1 iso C | 1.43 | 4.28 |
| 17:1 anteiso C | 2.67 | 2.01 |
| 17:1 cis9 | 0.00 | 0.73 |

TABLE 4

Carbohydrate utilization patterns of strains ATCC# PTA-5316 (MA7327) and ATCC#PTA-5317 (MA7331)

| Carbon source | MA7327 | MA7331 |
|---|---|---|
| D-glucose | 3 | 2 |
| L-arabinose | 1 | 1 |
| Sucrose | 3 | 3 |
| D-xylose | 2 | 3 |
| I-inositol | 3 | 3 |
| D-mannitol | 3 | 2 |
| D-fructose | 3 | 3 |
| Rhamnose | 0 | 0 |
| Raffinose | 3 | 3 |
| Cellulose | 1 | 0 |

Growth of the culture was monitored using compounds in the table as a carbon source: Observations were made at 7, 14 and 21 days intervals and 28° C. and utilization of the respective carbon sources are listed below. Growth levels: 3=good utilization; 2=moderate utilization; 1=poor utilization; 0=no utilization.

Example 2

Production of Compound II

TABLE 5

Media Composition

| Component | g/L |
|---|---|
| SEED Media composition: | |
| Soluble starch | 20 |
| Dextrose | 10 |
| NZ Amine type E | 5 |
| Difco Beef Extract | 3 |
| Bacto (Difco) Peptone | 5 |
| Difco Yeast Extract | 5 |
| CaCO3 | 1 |
| YME.TE (Production Medium, g/l) | |
| Media Component | |
| *Difco yeast extract | 6 |
| *Malt extract | 15 |
| *Dextrose | 6 |
| Trace Elements | 5 ml |
| MOPS | 20 | pH = 7.0

A frozen suspension (1.3 mL) of a *Streptomyces* sp. ATCC# PTA-5942 (MA7339) was inoculated into a 250 mL flask containing 50 mL of seed medium. The flask was incubated at 28.0° C. with an agitation of 220 RPM for 48 hours. The second stage seed was developed by transferring 3% inoculum of the first stage seed into a 250 ml shake flask containing 50 mL of seed medium. The flask was incubated at 28.0° C. with an agitation of 220 RPM for 24 hours. A 5% inoculum of the second stage seed was transferred to 30 ml of YME-TE in a 250 ml and incubated at 32.0° C. with an agitation of 220 RPM for 12 days.

Isolation of Compound II

To a two liter fermentation broth was added two liter of acetone and shaken on a shaker for two hours and filtered. The filtrate was concentrated under reduced pressure to remove most of the acetone and charged on to a 75 mL amberchrome (CG161s) column. The column was eluted with a gradient of 90% water to 100% methanol that eluted the compound in a broad zone which upon concentration and lyophilization afforded 170 mg of semi-purified fraction. A 80 mg portion of the fraction was purified by prep HPLC (Zorbax Rx C8 21.4× 250 mm with a gradient of 20-98% aqueous acetonitrile containing 0.1% trifluoroacetic acid to produce 1.1 mg of compound I. The structure was elucidated by spectroscopic analysis (see below).

Physical Data of Compound II

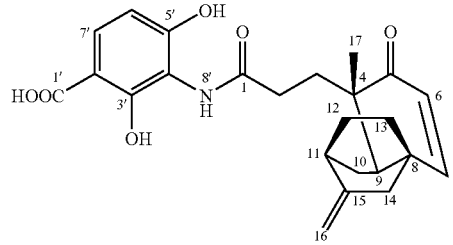

| | |
|---|---|
| MW | 425 |
| MF | $C_{24}H_{27}NO_6$ |
| HEESIFTMS | Found: 426.1911; calcd for M + H: 426.1911 |
| $[\alpha]^{23}_D$ | +2.1° (c 0.96, $CH_3OH$) |
| UV ($CH_3OH$) $\lambda_{max}$ | 226 ($\epsilon$ 16,837) 296 (2,663) nm |

TABLE 6

$^1H$ and $^{13}C$ NMR Assignment of Compound I at 500 MHz

| # | $C_5D_5N$ $^{13}C$ | Type | $C_5D_5N$ $^1H$ |
|---|---|---|---|
| 1 | 175.2 | ° C. | |
| 2 | 32.2 | $CH_2$ | 2.70, m |
| 3 | 31.8 | $CH_2$ | 2.53, m |
| | | | 1.92, m |
| 4 | 48.1 | ° C. | |
| 5 | 204.1 | ° C. | |
| 6 | 126.8 | CH | 5.92, d, 10.0 |
| 7 | 154.9 | CH | 6.36, d, 10.0 |
| 8 | 36.7 | ° C. | |
| 9 | 40.4 | CH | 2.00, t, 10.2 |
| 10 | 27.1 | $CH_2$ | 1.60, m |
| | | | 1.36, brt, 10.2 |
| 11 | 36.6 | CH | 2.26, m |
| 12 | 26.5 | $CH_2$ | 1.78, m |
| | | | 1.56, m |
| 13 | 28.5 | $CH_2$ | 1.56, t, 7.8 |
| | | | 1.80, m |
| 14 | 44.9 | CH | 1.93, d, 10.2 |
| | | | 2.15, d, 10.2 |
| 15 | 149.8 | ° C. | |

TABLE 6-continued

¹H and ¹³C NMR Assignment of Compound I at 500 MHz

| # | C$_5$D$_5$N ¹³C | Type | C$_5$D$_5$N ¹H |
|---|---|---|---|
| 16 | 107.8 | CH$_2$ | 4.71, brs |
|  |  |  | 4.87, brs |
| 17 | 21.5 | CH$_3$ | 1.09, s |
| 1' | 175.2 | °C. |  |
| 2' | 107.6 | °C. |  |
| 3' | 158.8 | °C. |  |
| 4' | 115.8 | °C. |  |
| 5' | 158.3 | °C. |  |
| 6' | 110.4 | CH | 6.88, d, 8.4 |
| 7' | 129.8 | CH | 8.12, d, 8.4 |
| 8' |  | NH | 10.50, s |
| 3'-OH |  |  |  |
| 5'-OH |  |  |  |

Characterization of Culture

General description of culture MA-7339 producer of compound II is described.

Observations of growth, general cultural characteristics and carbon source utilization were made in accordance with the methods of Shirling and Gottlieb (*Int. J. Syst. Bacteriol.* (1966) 16: 313-340). Coloration of the cultures was determined by comparison with color standards contained in the Methuen Handbook of Colour (A. Kornerup and J. H. Wauscher, Third Edition, 1978).

Chemical composition of the cells was determined using the methods of Lechevalier and Lechevalier (1980).

Fatty acid composition was determined using a modified sample preparation (Sasser, 1990). Analysis of fatty acid methyl esters (FAMEs) was carried out by capillary gas chromatography using a Hewlett Packard Model 6890N gas chromatograph/Microbial Identification System software (MIDI, Inc., Newark, Del.) equipped with a phenyl methyl silicone column (0.2 mm×25 m). Individual fatty acids identification was determined by the Microbial Identification System software.

Source:

Strain MA7339 was obtained from a soil collected in Mallorca, Balearic Islands, Spain. The strain was isolated after pretreatment of the soil with 1% (w/v) chloramine T and plating on humic-acid based agar supplemented with 20 ug/ml nalidixic acid. After purification on Yeast Malt Extract agar, the isolate was detected active when tested as agar plug in the FabF_SPAR_C screen.

General Growth Characteristics.

Strain MA7339 grows well on a range of agar media such as Yeast Malt Extract, Oatmeal, Glycerol Asparagine, Inorganic Salts Starch and Trypticase Soy agars at 28° C. The gross colonial morphology is typical of streptomycetes and its growth characteristics, including spore-mass colour, substrate mycelial pigmentation and the production of different pigments were recorded in different agar media (Table 7).

Colony morphology (on Yeast Malt Extract Agar, ISP2): Substrate mycelium initially whitish yellow turns yellowish brown (5D7) after 21 days of incubation. The initial white aerial mycelium continues to develop after 21 days incubation turning whitish grey (5E1/5E2) with brownish wet exudate droplets.

Micromorphology: the spore-chain morphology was examined directly on the plates by light microscopy under 400× and 1000× magnification. Observations were made after 7, 14 and 21 days of cultivation on Yeast Malt Extract agar. The aerial mycelium arises from extensive branched substrate hyphae. Sparse branched aerial hyphae differentiate initially into short and irregularly tight coiled spore chain spirals. Sporophores are formed by less than 10-20 spores and with time tend to coalesce in a dark mucous mass of spores in older cultures. Similar morphologies were observed in most of the other test media but with different degrees of coalescence. On the contrary in the glycerol asparagine agar the strain grows as a sterile vegetative mycelium.

Chemotaxonomic Analysis.

The analysis of cell wall composition shows that strain MA7339 contains LL-A2pm in whole-organism hydrolysates, a characteristic of *Streptomyces*, and glucose and ribose as major cell wall sugars. The strain is rich in saturated straight-chain and iso- and anteiso-fatty acids and whole-cell methanolysates contain the predominant fatty acids 15:0 anteiso (12.43%) and 16:0 iso (17.94%), which are also typical of *Streptomyces*. Nevertheless the major component is the fatty acid species 15:0 iso (20.43%). A complete fatty acid composition is given in Table 8.

All these chemotaxonomic analyses indicate that the strain corresponds to a member of the genus *Streptomyces*.

Physiological Properties.

Strain MA7339 presents the following carbon utilization pattern (Table 9):

good utilization of sucrose, D-xylose, D-fructose and raffinose; moderate utilization of D-glucose, 1-inositol, and D-mannitol; and no utilization of L-arabinose, cellulose and rhamnose.

16S rDNA Sequence and Phylogenetic Analysis.

The complete 16S rDNA sequence has been determined for strain MA-7339. Sequence was aligned with *Streptomyces* nucleotide sequences from Genbank (AB045882) and the *S. platensis* strains MA7327 and MA7331. A phylogenetic tree based on these 16S rDNA sequences was built using the maximum parsimony method. Bootstrap replicates from each grouping was used as a measure of statistical confidence. A grouping found on 95% of bootstrap replicates was considered statistically significant.

The strain MA7339 is associated to the strain *Streptomyces platensis* ATCC 13865 and the strains MA7327 and MA7331. This close relationship is highly supported by the bootstrapping value (97%) and suggests that this isolate can be identified as another strain of the species *Streptomyces platensis*.

TABLE 7

Cultural characteristics of *Streptomyces* sp. MA7339 (21 days, 28° C.)

| Medium | Amount of growth | Aerial Mycelium | Soluble pigments | Substrate Mycelium |
|---|---|---|---|---|
| Yeast Extract Malt Extract (ISP2) | Abundant | Whitish grey (5E1/5E2), dense growth, extensive aerial mycelium with short and tight irregular spore chains forming loops and coils. Sporophores | None | Yellowish brown (5D7) |

TABLE 7-continued

Cultural characteristics of *Streptomyces* sp. MA7339 (21 days, 28° C.)

| Medium | Amount of growth | Aerial Mycelium | Soluble pigments | Substrate Mycelium |
|---|---|---|---|---|
| Oatmeal (ISP3) | Abundant | born in main and secondary aerial branches, coalescence. Grey (5E2/F2), extensive aerial mycelium, coalescence of tight coiled spore chains. | None | Olive brown (4E3) |
| Inorganic Salts Starch (ISP4) | Abundant | Greyish brown (5D3/F3), extensive aerial mycelium, coalescence of chains. | None | Light yellow (4A4) |
| Glycerol Asparagine (ISP5) | Sparse | none | None | Greyish orange(5B4), sterile substrate mycelium |
| Tyrosine Agar (ISP7) | Abundant | Orange grey (5B2), extensive aerial mycelium growth, short and tight spirals in aerial hyphae, collapsing in coalescence and knots | none | Dark brown (6F7) |

TABLE 8

Major fatty acids found in strain MA7339.

| Fatty acid | % of total fatty acids |
|---|---|
| 14:0 iso | 5.66 |
| 15:0 iso | 20.43 |
| 15:0 anteiso | 12.43 |
| 15:0 anteiso 2OH | 8.00 |
| 15:0 | 3.48 |
| 16::0 | 2.52 |
| 16:0 iso | 17.94 |
| 16:1 iso H | 3.54 |
| 16:0 iso 2OH | 1.14 |
| 17:0 anteiso | 3.58 |
| 17:0 cyclo | 1.48 |
| 17:0 iso | 3.36 |
| 17:1 iso C | 2.28 |
| 17:1 anteiso C | 2.28 |

TABLE 9

Carbohydrate utilization patterns of strains MA7339.

| Carbon source | Growth levels |
|---|---|
| D-glucose | 2 |
| L-arabinose | 0 |
| Sucrose | 3 |
| D-xylose | 3 |
| I-inositol | 2 |
| D-mannitol | 2 |
| D-fructose | 3 |
| Rhamnose | 0 |
| Raffinose | 3 |
| Cellulose | 0 |

Growth on the following compounds as sole carbon sources; Observations were made at 7, 14 and 21 days, 28° C.; Growth levels: 3=good utilization; 2=moderate utilization; 1=poor utilization; 0=no utilization.

Example 3

Compounds with formula I (platensimycin) and II (platencin) were titrated against human or rat FAS using the Flashplate assay. Animal FAS activity was assayed radiochemically for the formation of $^3$H-palmitate. The assay buffer contained 200 mM KPi, pH 7, 2 mM EDTA, 2.5 mM DTT, 5 μM Acetyl CoA ($^3$H-acetyl-CoA, Specific Activity=0.3 Ci/mmole), 21 μM malonyl-CoA, and 20 uM NADPH in a final reaction volume of 200 μl. Assays are performed in 96-well Phospholipid coated FlashPlates (Perkin Elmer). The reaction was initiated by adding FAS (0.17 mUnits/well, 1 Unit=1μ mole of NADPH consumed/minute). The plates were incubated at RT for 5 minutes before adding 6 μl of perchloric acid to stop the reaction. The plates sat at RT for at least 3 hours, preferably overnight, before counting. Background was determined from wells without malonyl CoA. The source of Human FAS was SkBr3 cells. Cell extracts were processed by ammonium sulfate precipitation followed by DEAE chromatography essentially as described by Jayakumar et al.,1995 (Jayakumar A, Tai M H, Huang W Y, al-Feel W, Hsu M, Abu-Elheiga L, Chirala S S, Wakil S J. Human fatty acid synthase: properties and molecular cloning. Proc Natl Acad Sci U S A. 1995 September 12; 92(19):8695-9). SkBr3 cells were selected as the source owing to their high levels of FAS expression as described by Thompson et al (Thompson B J, Stem A, Smith S. Purification and properties of fatty acid synthetase from a human breast cell line. Biochim Biophys Acta. 1981 Nov. 13; 662(1):125-30). The source of rat FAS was liver from fasted and high carbohydrate re-fed rats as described by Linn (Linn T C. Purification and crystallization of rat liver fatty acid synthetase. Arch Biochem Biophys. 1981 July; 209(2):613-9). Livers were homogenized in lysis buffer (100 mM KPi, pH 7.4, 150 mM NaCl, 1 mM EDTA, 10% Glycerol, Sigma mammalian protease inhibitors at 5 ug/ml) using a Waring blender. The homogenate was centrifuged at 3000×g and then at 100000×g. The clarified supernatant was fractionated by ammonium sulfate precipitation. The fraction between 25% and 36% was subject to DEAE sepahaorse chromatography essentially as described by Jayakumar et al., 1995.

TABLE 10

FAS inhibitory activity by formula I and II in cell free flash plate assay

| Compound | Human IC$_{50}$ (μM) | Rat IC$_{50}$ (μM) |
|---|---|---|
| Formula I | 0.30 | 0.18 |
| Formula II | 6.3 | |

Determination of Fatty Acid and Sterol Synthesis and Fatty Acid Oxidation in Rat Hepatocytes In Vitro Primary hepatocytes were prepared from male CD rats (250 g) and plated overnight on Primaria 6 well plates in hepatocytes attachment medium with 10% fetal calf serum at a density of $0.8 \times 10^6$ cells/well. The cells were washed twice with PBS, and added with 2 ml DMEM high glucose medium. Fatty acid and sterol synthesis in the hepatocytes were measured as described previously (Jiang G, Li Z, Liu F, Ellsworth K, Dallas-Yang Q, Wu M, Ronan J, Essau C, Murphy C, Szalkowski D, Bergeron R, Doebber T and Zhang B. Prevention of obesity in mice by antisense oligonucleotide inhibitors of stearoyl-CoA desaturase-1. J. Clin. Invest. 115: 1030-1038 (2003); Jiang G, Li Z, Liu F, Ellsworth K, Dallas-Yang Q, Wu M, Ronan J, Essau C, Murphy C, Szalkowski D, Bergeron R, Doebber T and Zhang B. Prevention of obesity in mice by antisense oligonucleotide inhibitors of stearoyl-CoA desaturase-1. J. Clin. Invest. 115: 1030-1038 (2003) with modifications. The cells pre-incubated with compounds in 5 μl DMSO for 60 min, then added C14-acetate (NEN) at 0.5 μci per well. The wells were gassed with $O_2$—$CO_2$ (95%-5%) and plates were sealed with parafilm for additional 2 hr incubation. After incubation, the cells were washed twice with PBS and mixed with 2.5 ml 10% KOH in methanol and 1.0 ml distilled water per well. The mixture was heated at 90 C for 3 hr, and extracted with 4 ml petroleum ether (PE). Three ml of upper PE layer was transferred into scintillation vial, dried under low heat, and then counted the level of C14-sterols. Three ml of lower aqueous layer was added 1.0 ml of 10M $H_2SO_4$ (PH<2.0), mixed well and then extracted with 4 ml of PE. The 3 ml of upper layer was dried under low heat, and counted the level of C14-fatty acid. Fatty acid oxidation in the hepatocytes was determined the conversion of C14-oleic acid to soluble acid products as described (Jiang G, Li Z, Liu F, Ellsworth K, Dallas-Yang Q, Wu M, Ronan J, Essau C, Murphy C, Szalkowski D, Bergeron R, Doebber T and Zhang B. Prevention of obesity in mice by antisense oligonucleotide inhibitors of stearoyl-CoA desaturase-1. J. Clin. Invest. 115: 1030-1038 (2003); Mannaerts G P, Debeer L J, Thomas J, and DeSchepper P J. Mitochondrial and proxisomal fatty acid oxidation in liver homogenates and isolated hepatocytes from control and clofibrate-treated rats. J. Biol. Chem. 254:4585-4595 (1979)) with modifications. Hepatocytes seeded overnight and washed twice with PBS and then pre-incubated with compounds in 5 μl of DMSO in 2 ml medium 199 plus 0.25% bovine serum albumin for 60 min. C14-oleic acid 0.25 μCi (NEN) was added to each well. The plates were gassed and sealed. After one hr incubation, 1 ml of medium was removed, mixed with 100 μl of 10% BSA and then 100 μl 60% $HClO_4$. After centrifugation, 1 ml of the solution was counted the level of soluble acid products.

TABLE 11

Fatty acid synthesis inhibitory activity by formula I and II in rat hepatocytes

| Compound | Rat $IC_{50}$ μM |
|---|---|
| Formula I | 0.093 |
| Formula II | 3.24 |

TABLE 12

Inhibition of Oxidation of Fatty Acids

| Compound | Rat Hepatocyte (% of control at 10 uM) |
|---|---|
| Formula I | 59.7 |
| Formula II | 66.0 |

Reduction of Plasma Glucose In Vivo

C57BL/6N mice were continuously infused with 600 ug/hr of Formula I (see Wang et al., 2006, Nature 441:358 for infusion protocol). Infusion for three days lead to reduction of plasma glucose by 63.9% as compared to vehicle control determined by using standard method. Inhibition of fatty acid results in the accumulation of malonyl CoA which in turn inhibits fatty acid oxidation leading to increased metabolism of glucose.

TABLE 13

Reduction of Plasma Glucose

| Compound | C57BL/6N Mice |
|---|---|
| Formula I | 63.9% from control |
| Formula II | Not tested |

What is claimed is:

1. A method of treating Type II diabetes comprising administration to a subject in need thereof a therapeutically effective amount of a compound of formula I or II

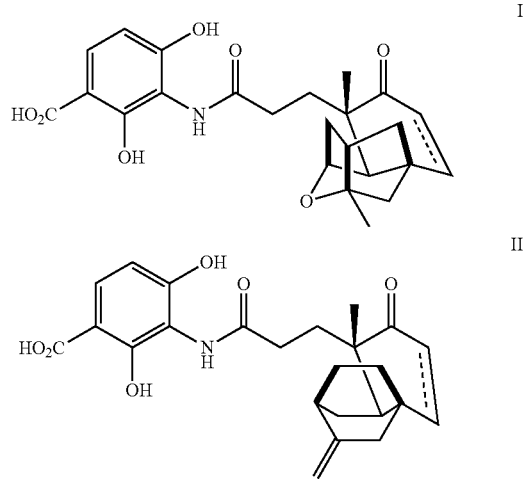

or a pharmaceutically acceptable salt thereof, wherein ----- represents a bond that can be absent or present.